United States Patent
Elsner et al.

(10) Patent No.: US 12,024,488 B2
(45) Date of Patent: Jul. 2, 2024

(54) PROCESS FOR HETEROGENEOUS ISOMERIZATION OF ALPHA-OLEFINS

(71) Applicant: Evonik Operations GmbH, Essen (DE)

(72) Inventors: Jens Elsner, Hochheim (DE); Horst-Werner Zanthoff, Muelheim a.d. Ruhr (DE); Fikri Sen, Oberhausen (DE)

(73) Assignee: Evonik Operations GmbH, Essen (DE)

( * ) Notice: Subject to any disclaimer, the term of this patent is extended or adjusted under 35 U.S.C. 154(b) by 161 days.

(21) Appl. No.: 17/755,905

(22) PCT Filed: Nov. 4, 2020

(86) PCT No.: PCT/EP2020/080935
§ 371 (c)(1),
(2) Date: May 11, 2022

(87) PCT Pub. No.: WO2021/094162
PCT Pub. Date: May 20, 2021

(65) Prior Publication Data
US 2022/0380276 A1    Dec. 1, 2022

(30) Foreign Application Priority Data

Nov. 14, 2019   (EP) ..................... 19209088

(51) Int. Cl.
*C07C 5/02*        (2006.01)
*B01J 21/12*       (2006.01)
*B01J 35/61*       (2024.01)
*C07C 5/25*        (2006.01)
*C07C 11/02*       (2006.01)

(52) U.S. Cl.
CPC ............ *C07C 5/2512* (2013.01); *B01J 21/12* (2013.01); *B01J 35/613* (2024.01); *B01J 35/615* (2024.01); *C07C 11/02* (2013.01); *C07C 2521/12* (2013.01)

(58) Field of Classification Search
CPC . B01J 21/12; B01J 35/10; C07C 11/02; C07C 5/25
See application file for complete search history.

(56) References Cited

U.S. PATENT DOCUMENTS 5,849,974 A    12/1998  Clarembeau et al.
6,281,404 B1    8/2001  Miller
(Continued)

FOREIGN PATENT DOCUMENTS

DE    198 47 161    4/2000
EP    0 396 763    11/1990
(Continued)

OTHER PUBLICATIONS

Extended European Search Report issued May 12, 2020, in European Patent Application No. 19209088.4, 6 pages.
(Continued)

*Primary Examiner* — Sharon Pregler
(74) *Attorney, Agent, or Firm* — Grüneberg and Myers PLLC

(57) ABSTRACT

A method for the isomerization of alpha-olefins to the corresponding internal olefins uses a heterogenous catalyst containing silicon-aluminum mixed oxide in a continuous fixed-bed operation mode.

24 Claims, 1 Drawing Sheet

Comparison of long-term stability tests ($^{13}$C-NMR) of the 1-tetradecene conversion in all reactors and experiments

(56) References Cited

U.S. PATENT DOCUMENTS

| | | | |
|---|---|---|---|
| 6,613,300 B2 | 9/2003 | Mangold et al. | |
| 8,575,081 B2 | 11/2013 | Miller et al. | |
| 8,980,784 B2 | 3/2015 | Schulze Isfort et al. | |
| 9,371,255 B2 | 6/2016 | Winterberg et al. | |
| 11,261,141 B2* | 3/2022 | Kramer | C09K 8/32 |
| 2005/0070747 A1* | 3/2005 | Brown | C07C 5/2518 |
| | | | 585/17 |
| 2009/0301345 A1 | 12/2009 | Mangold et al. | |
| 2020/0325085 A1* | 10/2020 | Kramer | B01J 21/04 |

FOREIGN PATENT DOCUMENTS

| | | |
|---|---|---|
| EP | 0 850 876 | 7/1998 |
| WO | 2005/031066 | 4/2005 |
| WO | 2009/085886 | 7/2009 |

OTHER PUBLICATIONS

International Search Report issued Jan. 20, 2021, in PCT/EP2020/080935, 5 pages.
Written Opinion issued Jan. 20, 2021, in PCT/EP2020/080935, 7 pages.
Li et al., "The Nature and Catalytic Function of Cation Sites in Zeolites: a Computational Perspective", CHEMCATCHEM Reviews, vol. 11, Jan. 9, 2019, pp. 134-156.

* cited by examiner

Comparison of long-term stability tests ($^{13}$C-NMR) of the 1-tetradecene conversion in all reactors and experiments
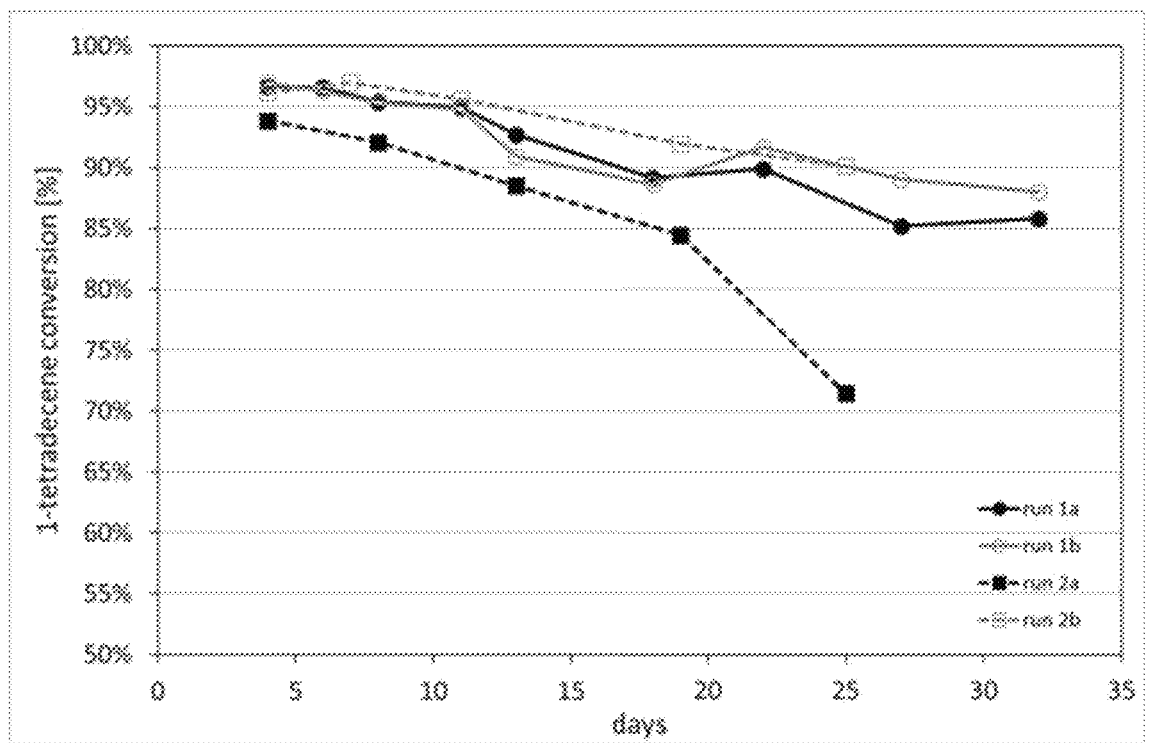

US 12,024,488 B2

PROCESS FOR HETEROGENEOUS ISOMERIZATION OF ALPHA-OLEFINS

CROSS-REFERENCE TO RELATED APPLICATIONS

This application is the National Stage entry under § 371 of International Application No. PCT/EP2020/080935, filed on Nov. 4, 2020, and which claims the benefit of priority to European Application No. 19209088.4, filed on Nov. 14, 2019. The content of each of these applications is hereby incorporated by reference in its entirety.

BACKGROUND OF THE INVENTION

Field of the Invention

The present invention is directed to a new method for the isomerization of alpha-olefins to the corresponding internal olefins by using a heterogenous catalyst comprising silicon-aluminum mixed oxide as catalyst in a continuous fixed-bed operation mode.

Description of Related Art

Alpha-olefins have a wide variety of end uses, mainly dependent on the chain length. There are certain applications, such as paper sizing agents and drilling fluids, which additionally require the use of internal olefins. Internal olefins may be produced from their corresponding alpha-olefins by isomerization processes. There are several catalysts known for the isomerization of alpha-olefins to internal olefins. Active catalysts can reach the thermodynamic isomerization limit, thereby giving internal olefins with an equilibrium distribution of double bond isomers.

The use of the generated and subsequently purified isomers can be epoxidation of the double bond, resulting in epoxides that can be polymerized in a second step to polyesters of different chain lengths for use as base oils or viscosity modifiers in various applications and formulations like lubricants. Another usage of the epoxides generated out of these isomers represents the formation of diesters that could also be used as low viscous base fluids in various applications and formulations.

Various catalysts are known for their use in the double bond isomerization of olefinic compounds. These are mainly zeolites and mole sieves as well as resin-type acidic systems (U.S. Pat. No. 5,849,974). However, many of these catalysts produce substantial amounts of polymer and/or skeletal isomerized product; i.e., branched olefins or dimers or oligomers. For some applications, it is desirable to limit branched products to the least amount possible. Therefore, for certain applications, it is desirable to use a catalyst which is selective for the isomerization of the double bond without the isomerization of the skeletal structure or the formation of dimers or higher oligomers. The formations of dimers and higher oligomers are side reactions of acidic catalyst systems. To avoid these side reactions, basic catalysts or catalysts doped with alkaline or earth alkaline metals are used.

U.S. Pat. No. 6,281,404 B1 relates to a process for the double bond isomerization of olefinic feed compounds in the presence of a molecular sieve of specific pore geometry. Such catalysts are described to be silica-containing alumino-phosphate molecular sieve which is usually referred to as a SAPO. In the working examples, SAPO-39 was used to isomerize 1-pentene at a temperature of 400° F. (204° C.). The conversion received was with up to 65% by weight quite low.

WO 2005/031066 relates to a process of converting compositions of C16 and or C18 alpha-olefins to internal olefins in the presence of a solid acid silica-alumina catalyst at an operating temperature from 70° C. to 140° C. It is reported that the isomerized internal olefin mixture contains less than 25% by weight of alpha-olefins and corresponding inner olefins having double bonds at positions 6-8. In the working examples, X-600 (a product of Criterion Catalyst Co.) was used to isomerize 1-hexadecene at temperatures of 70° C., 100° C. and 120° C. A disadvantage of this process is that the catalyst needs to be activated at high temperatures (about 350° C.) before the isomerization (see e.g. Example 1).

WO 2009/085886 relates to a process for the isomerization of alpha-olefins to internal olefins in the presence of a SAPO catalyst. However, the activity of the catalyst is low (WHSV<0.7).

U.S. Pat. No. 8,575,081 B2 relates to methods of making diester-based lubricant compositions. As starting material an olefin is used which can be an alpha-olefin or an isomerized olefin with inner double bonds. Such isomerizations are described to be carried out catalytically using a catalyst such as crystalline aluminosilicate and aluminophosphates. However, any specific isomerization using the catalyst according to the present invention is not disclosed therein.

U.S. Pat. No. 8,980,784 B2 relates to silicon-aluminum mixed oxides and their use as catalysts in the gas-phase dissociation of methyl tert-butyl ether (MTBE). The isomerization of alpha-olefins is not disclosed therein.

U.S. Pat. No. 9,371,255 relates to mixed oxide compositions, the use thereof as catalysts for the cleavage of alkyl tert-alkyl ethers or tertiary alcohols, and to a process for cleaving alkyl tert-alkyl ethers or tertiary alcohols to iso-olefins and alcohol or water. However, the isomerization of alpha-olefins is not disclosed.

Generally, the method(s) for producing isomerized olefins may be conducted using reaction conditions which can provide an olefin product having the desired features. Isomerization reaction conditions which may be utilized and variated to form a desired olefin product include reaction temperature, weight hourly space velocity, reaction pressure, conversion of the olefin feedstock to an isomerized olefin, amount of skeletally isomerized olefin found in the reactor effluent, and the presence or absence of a solvent or diluent, among others.

The known isomerization catalysts and respective processes have at least one of the following disadvantages:
  (a) Low conversion rate of the alpha-olefin into internal olefins to make a process economically advantageous and cost-effective.
  (b) Varying distribution of internal olefins over the carbon chain. That means that the receipt of a product with a consistent quality, i.e. with a uniform distribution of the isomerized products, cannot be constantly prepared.
  (c) Formation of undesirable by-products such as high concentration of dimer in the product which have to be removed in a subsequent cleaning step.
  (d) Short operating life-time of the catalyst.
  (e) High temperature treatment or other specific procedures are necessary to activate the catalyst.
  (f) Recycling of the catalyst is often not possible or delivers substantial different product mix.
  (g) Catalyst needs frequent reactivation (e.g. in air).

SUMMARY OF THE INVENTION

It was therefore an object of the present invention to provide a method for the isomerization of alpha-olefins in the presence of a catalyst by means of which the above-mentioned disadvantages can be minimized or entirely avoided.

It was now surprisingly found that the technical object is achieved by a method for the isomerization of alpha-olefins using a catalyst with medium or low acidity, such as the heterogenous catalyst comprising silicon-aluminum mixed oxide as catalyst described in this application. Such method provides promising results in double bond isomerization with minimized side reactions such as branching and oligomerization and can be run in a batch or continuous fixed-bed operation mode, preferably in a continuous fixed-bed operation mode. This method can also be run in a continuous slurry reactor.

BRIEF DESCRIPTION OF THE DRAWING

The FIGURE shows a comparison of the 1-tetradecene conversion in described reactors and experiments.

DETAILED DESCRIPTION OF THE INVENTION

One embodiment of the present invention is directed to a method for converting alpha-olefins to isomerized products by using a silicon-aluminum mixed oxide as catalyst. The method is preferably carried out in a continuous fixed-bed operation mode.

The isomerized products contain internal unsaturated bonds (i.e. they are internal olefins) and only small amounts of dimers. Preferably, the conversion rate of alpha-olefins to isomerized products is 95% or higher. The amount of dimers in the isomerized product(s) is preferably 5 mol % or lower.

The mixed oxides used as catalyst in the present invention are prepared in the manner of flame hydrolysis as described in DE 198 47 161 A1 or EP 0850 876 A1.

In this so-called "co-fumed process", volatile silicon and aluminium compounds, usually silicon tetrachloride and aluminium trichloride, are injected into an explosive gas flame of hydrogen and oxygen or air. The volatile silicon and aluminium compounds are hydrolysed by the water formed in the explosive gas flame to form the mixed oxide.

An alternative also disclosed in the above-mentioned documents is the doping process. Therein, an aerosol is fed into a hydrogen/oxygen gas flame in which an oxide, e.g. silicon oxide as in the present case, is obtained from a volatile compound, e.g. silicon tetrachloride, by flame hydrolysis, said aerosol containing a salt of the element to be doped, e.g. aluminium, and the corresponding mixed oxide thus being formed. The silicon-aluminium mixed oxide prepared by flame hydrolysis is predominantly or entirely amorphous.

The silicon-aluminium mixed oxide prepared by the aforementioned methods are characterised by high purity and have the following composition:
  (a) 75 bis 99.99% by weight, preferably 85 to 99.99% by weight, more preferably 95 to 99.9% by weight, and even more preferably 97 to 99.9% by weight, of silicon oxide (calculated as $SiO_2$); and
  (b) 0.01 to 25% by weight, preferably 0.01 to 15% by weight, more preferably 0.1 to 5% by weight, and even more preferably 0.1 to 3% by weight of aluminum oxide (calculated as $Al_2O_3$).

In a further embodiment, the silicon-aluminum mixed oxide does additionally contain alkali or earth alkaline metal oxides, preferably in an amount of up to 1% by weight, based on the total composition of the silicon-aluminum mixed oxide.

To introduce the alkali metals or alkaline earth metals, the mixed oxide produced by flame hydrolysis can be treated with aqueous solution of alkali metal or alkaline earth metal hydroxide. This can be affected, for example, by impregnating the mixed oxide produced by flame hydrolysis with an alkali metal and/or alkaline earth metal salt solution. Subsequently, the resulting mixed oxide is washed with water, dried at 100 to 150° C. and calcined at 300 to 600° C., preferably at 450 to 550° C.

The silicon-aluminum mixed oxide may also contain traces of alkali metal or alkaline earth metals which are not considered in the context of the present invention.

A further embodiment of the present invention is directed to silicon-aluminum mixed oxides which are further treated with an acidic, aqueous phosphorus source. The phosphorus source used may be phosphoric acid, phosphonic acid, phosphinic acid, polyphosphoric acid or dihydrogen phosphate, preferably phosphoric acid. The treatment is affected by suspending the mixed oxide composition in water and admixing this suspension with the phosphorus source, such that a pH of 0 to 6, preferably of 1 to 2.5, and more preferably of 2 to 2.5, is established. Subsequently, the treated catalyst is washed with water, dried at 100 to 150° C. and calcined at 300 to 600° C., preferably at 450 to 550° C.

In a further embodiment, the silicon-aluminum mixed oxide composition is notably present predominantly (means<70%) or completely in the form of aggregated primary particles.

The silicon-aluminum mixed oxide composition according to the present invention is inter alia characterized in that the weight ratio $(Al_2O_3/SiO_2)_{surface}$ of the primary particles in a layer close to the surface is lower than in the weight ratio $(Al_2O_3/SiO_2)_{total}$ of the overall primary particles. The term "layer close to the surface" means the area from the surface until a depth of 5 nm.

The difference in the weight ratios means that the aluminium oxide concentration at the surface is lower than in the overall composition. The overall primary particle also includes the proportion of silicon dioxide and aluminium oxide in the layer close to the surface.

In a further embodiment, the silicon-aluminum mixed oxide composition is present predominantly or entirely in the form of aggregated primary particles, characterized in that
  (a) the weight ratio of $(Al_2O_3/SiO_2)_{total}$ in the total primary particle is from 0.002 to 0.05, preferably 0.003 to 0.015, and more preferably 0.005 to 0.01; and
  (b) the weight ratio $(Al_2O_3/SiO_2)_{surface}$ of the primary particles in a layer close to the surface is lower than in the overall primary particle.

For the purposes of the present invention, a mixed oxide is an intimate mixture of the mixed oxide components aluminum oxide and silicon dioxide at an atomic level, in which the primary particles also have Si—O—Al bonds. The surfaces of these primary particles are largely or completely free of pores.

The weight ratio $(Al_2O_3/SiO_2)_{surface}$ on the surface can be determined, for example, by X-ray-induced photoelectron spectroscopy (XPS analysis) of the powder. Additional information on the surface composition can be obtained by energy-dispersive X-ray analysis (TEM-EDX analysis) of individual primary particles.

The weight ratio $(Al_2O_3/SiO_2)_{total}$ in the total primary particle is determined by chemical or physicochemical methods, e.g. X-ray fluorescence analysis of the powder.

The silicon-aluminum mixed oxide composition can be further characterized in that:

(c) the BET surface area is from 50 to 250 m²/g, preferably from 100 to 200 m²/g (determined to DIN ISO 9277 (status: 2014-01).

It has been further found that it can be advantageous for the silicon-aluminum mixed oxide to have a dibutyl phthalate number, in g of dibutyl phthalate (DBP)/100 g of mixed oxide, of from 300 to 350. The DBP number is a measure of the structure of aggregates. Low numbers correspond to a low-level structure, while high numbers correspond to a high-level structure. The preferred range from 300 to 350 corresponds to a high-level structure. In DBP absorption, the force taken up, for example the torque (in Nm), by the rotating blades of the DBP measurement instrument on addition of defined amounts of DBP, comparable to a titration, is measured. Here, the silicon-aluminum mixed oxide according to the invention displays a sharply pronounced maximum with a subsequent decrease at a particular addition of DBP. The dibutyl phthalate absorption can be measured, for example, using a RHEOCORD 90 instrument from Haake, Karlsruhe. For this purpose, 12 g of the silicon-aluminum mixed oxide powder are weighed out to within 0.001 g and introduced into a kneading chamber, the latter is closed by means of a lid and dibutyl phthalate is metered in through a hole in the lid at a predetermined metering rate of 0.0667 ml/s. The kneader is operated at a motor speed of 125 revolutions per minute. After the torque maximum has been reached, the kneader and the introduction of DBP are automatically switched off. The DBP absorption is calculated from the amount of DBP consumed and the amount of particles weighed according to: DBP number (g/100 g)=(consumption of DBP in g/weight of powdering)×100.

The silicon-aluminum mixed oxide composition can be applied to a support, for example a metal, polymer or ceramic support, which is inert in relation to the isomerization reaction in which the catalyst is to be used. When the inventive catalyst has been applied to an inner support, the mass and composition of the inert support are not taken into account in the determination of the composition of the silicon-aluminum mixed oxide.

The olefin feedstock used in accordance with the present invention is selected from an alpha-olefin comprising 10 to 20 carbon atoms, preferably 14 to 16 carbon atoms and most preferably 14 carbon atoms. The invention is not limited to feedstocks comprising a single component, but also mixtures of more than one component also with different chain length may be used. In a further embodiment, the olefin feedstock is an alpha-tetradecene comprising at least 90% by weight of mono-olefinic linear alpha-olefins.

One source of commercially available alpha-olefins is the oligomerization of ethylene. A second source of commercially available alpha-olefin products is Fischer-Tropsch synthesis streams. One source of commercially available normal alpha-olefin products produced by ethylene oligomerization which may be utilized as an olefin feedstock is Chevron Phillips Chemical Company LP, The Woodlands, TX. Other sources of commercially available normal alpha-olefin products produced by ethylene oligomerization which may be utilized as an olefin feedstock include Ineos Oligomers (Feluy, Belgium), Shell Chemicals Corporation (Houston, TX or London, United Kingdom), Idemitsu Kosan (Tokyo, Japan), and Mitsubishi Chemical Corporation (Tokyo, Japan), among others. One source of commercially available normal alpha-olefin products produced, and optionally isolated from Fisher-Tropsch synthesis streams, includes Sasol (Johannesburg, South Africa), among others.

One embodiment of the present invention is directed to the method for the isomerization of alpha-olefins by using a silicon-aluminum mixed oxide as catalyst, the method comprising the steps of:

(a) providing the alpha-olefin and a catalyst in a reactor;
(b) inerting the reactor;
(c) adjusting the pressure in the reactor;
(d) heating the reactor to the desired reaction temperature;
(e) stirring the reaction mixture until the end of the mean reaction time;
(f) cooling the reaction mixture to a desired temperature for further processing;
(g) optionally filtering the catalyst from the reaction mixture by appropriate technology;
(h) optionally collecting the isomerized product; and/or
(i) optionally removing undesired by-products, e.g. by distillation, rectification, vacuum-distillation, membrane separation or other appropriate separation technologies.

The reactor can be selected form the group consisting of fixed bed reactors, slurry reactors or trickle-bed reactors.

For the variant of conducting the reaction in fixed bed reactors, it is necessary that the silicon-aluminum mixed oxide composition used as catalyst and produced by flame hydrolysis or pyrogenic means is subjected, with addition of a binder, to a shaping process, as sufficiently well known in the prior art, for example in the form of granules, pellets or shaped bodies, for example tablets, cylinders, spheres, extrudates or rings or more specific geometries obtained by additive manufactured processes, e.g. 3D printing. Suitable binders are known in the art, like for example aluminas, ceramic clays, colloids or amorphous zeolites which do not significantly influence the catalytic performance.

For the shaping process, 1 to 20% by weight of the silicon-aluminum mixed oxide composition is vigorously mixed with a binder as specified above, together with temporary assistants, for example water, aqueous solutions, water substitutes like glycols or polyglycols, and additionally fixatives, for example cellulose ethers, plasticizers, for example polysaccharides, and/or pressing aids, for example nonionic wax dispersions. This operation can be affected, for example, in a kneader or intensive mixer. Subsequently, a shaping process, for example pelletization, extrusion or dry pressing, produces the shaped bodies for the fixed bed reactor. Prior to the incorporation, the shaped bodies are calcined within a temperature range of 200 to 700° C., which removes at least the temporary assistants.

In one embodiment, the pressure in the reactor can be in the range of 2 to 6 bar, preferably in the range of 4 to 6 bar, more preferably in the range of 4.5 to 5 bar.

In one embodiment, the reaction temperature can be in the range of 130 to 340° C., preferably in the range of 150 to 200° C., more preferably in the range of 160 to 190° C.

In one embodiment, the mean reaction time can be in the range of 150 to 350 minutes, preferably in the range of 200 to 300 minutes, more preferably in the range of 230 to 260 minutes.

A further embodiment of the present invention is directed to the method for the isomerization of alpha-olefins in a continuous operation mode by using a silicon-aluminum mixed oxide as catalyst, the method comprising the steps of:

(a) providing the catalyst in a reaction zone, preferably in a fixed-bed reactor;

(b) inerting and tempering the reactor to the desired reaction temperature;
(c) continuously feeding the alpha-olefins first through a preheating zone and then through the reaction zone, preferably from the bottom to the top, by controlling temperature, pressure and weight hour space velocity (WHSV);
(d) optionally, in case of the use of slurry reactors, removing the catalyst from the reaction mixture at the reaction outlet;
(e) cooling the reaction mixture after the reaction zone to a desired temperature for further processing;
(f) optionally collecting the isomerized product; and/or
(g) optionally removal of undesired by-products, e.g. by distillation, rectification, vacuum-distillation or membrane separation.

The reactor can be selected from the group consisting of plug flow- or continuously stirred-type reactors (CSTR), and combinations thereof.

In one embodiment, a reactor filled with reaction mixture and free flowing powdered catalyst (slurry reactor) can be used. The educt is fed from the bottom and the reaction mixture is removed from the top, the catalyst being retained e.g. by filter elements. The reaction zone may comprise an internal or external recycle.

In a further embodiment, a tubular reactor with a catalyst fixed bed is applied. The educt can be fed by either from the bottom or the top.

In a further embodiment, continuously stirred-type reactors, e.g. vessels with a fixed bed of catalyst (e.g. Berty-type or Carberry-type reactors) or tubular fixed bed reactors with external recycle (e.g. loop reactors), can be used.

In a further embodiment, it might be favorable to combine a continuously stirred-type reactor with a tubular fixed bed as a finishing reactor.

In one embodiment, the catalyst consists of shaped bodies prepared by a shaping process from silicon-aluminum mixed oxide composition, binders and temporary assistants.

In one embodiment, the reaction temperature can be in the range of 130 to 340° C., preferably in the range of 150 to 200° C., more preferably in the range of 160 to 190° C.

In one embodiment, the weight hour space velocity (WHSV) is in the range of 3.0 to 5.5 $h^{-1}$, preferably in the range of 3.1 to 4.7 $h^{-1}$, and most preferably in the range of 3.5 to 3.7 $h^{-1}$.

Weight hourly space velocity (WHSV) is defined as the weight of feed flowing per hour per unit weight of the catalyst. Since weight of the catalyst charged into the reactor is not varied and always the same, any variation in flow of liquid per hour will change the WHSV. Inverse of the hourly space velocity is the specific residence time, i.e. how much time the liquid is in contact with the catalyst volume under the conditions of operation.

One of ordinary skill in the art recognizes that there is a relationship between the isomerization reaction temperature and the weight hourly space velocity. Generally, to obtain an isomerized product having equivalent features, an increase in the weight hourly space velocity will require an increase in the isomerization reaction temperature. Additionally, one of ordinary skill in the art recognizes that as the time the catalyst ages, the isomerization reaction temperature must be increased and/or the weight hourly space velocity must be decreased to maintain an olefin reactor effluent having the desired features.

Generally, the reactor effluent comprises an isomerized product. The isomerized product may further comprise isomerized olefins and/or skeletally isomerized olefins. The olefins which exit the reactor may include non-isomerized olefin, isomerized olefin, and/or skeletally isomerized olefin as well as oligomerized olefins. Oligomerized olefins comprise two or more units of the used feed, i.e. dimers, trimers or higher isomers of the used feed. The non-isomerized olefin, isomerized olefin, and skeletally isomerized olefins as well as oligomerized olefins, which may be present in the olefin reactor effluent, are independently described herein. Additionally, the quantities of non-isomerized olefin, isomerized product, isomerized olefin, skeletally isomerized olefin, as well as oligomerized olefins, which may be found in the olefin reactor effluent, are independently described herein and may be utilized in any combination to describe the olefin reactor effluent of the method(s) described herein.

The method as described further above is characterized by a conversion rate of alpha-olefin to the corresponding inner olefins of 90% or higher, preferably 95% or higher.

The amount of dimer is preferably 7 mol % or lower, more preferably 5 mol % or lower.

One embodiment is directed to the isomerized products of alpha-olefins comprising 10 to 20 carbon atoms, preferably 14 to 16 carbon atoms and most preferably 14 carbon atoms, and mixtures thereof, prepared by a method as outlined further above.

One embodiment is directed to the isomerized products of alpha-olefins comprising 10 to 20 carbon atoms, preferably 14 to 16 carbon atoms and most preferably 14 carbon atoms, and mixtures thereof, prepared by a method comprising the steps of:
(a) providing the catalyst in a reaction zone, preferably in a fixed-bed reactor;
(b) inerting and tempering the reactor to the desired reaction temperature;
(c) continuously feeding the alpha-olefins first through a preheating zone and then through the reaction zone, preferably from the bottom to the top, by controlling temperature, pressure and weight hour space velocity (WHSV);
(d) optionally, in case of the use of slurry reactors, removing the catalyst from the reaction mixture at the reaction outlet;
(e) cooling the reaction mixture after the reaction zone to a desired temperature for further processing;
(f) optionally collecting the isomerized product; and/or
(g) optionally removal of undesired by-products, e.g. by distillation, rectification, vacuum-distillation or membrane separation.

The FIGURE: Comparison of the 1-tetradecene conversion in all reactors and experiments. The analytical data were determined by using the $^{13}$C-NMR method.

The invention will be illustrated in detail below by examples and comparative examples without any intention that the concept of the invention be restricted to these particular embodiments.

Experimental Part $^{13}$C-NMR spectroscopical determination of the tetradecene isomer distribution The isomers produced by the isomerization of alpha-tetradecene were determined and quantified using offline $^{13}$C-NMR spectroscopy. The determination was carried out on CDCl3 with an addition of chromoacetylacetonate as relaxation aid. The double bond signals were used for the evaluation. Under the chosen conditions, resulting 5-, 6- and 7-tetradecenes could not be differentiated and are therefore given as a lumped value.

For further validation of the multiplicity of the signals, especially of the methylene and quaternary carbon atoms, $^{13}$C-DEPT spectrum was recorded as well.

Preparation of the Silicon-Aluminum Mixed Oxide

The vapor of a mixture consisting of 45 kg/h of CH$_3$SiCl$_3$ and 15 kg/h of SiCl$_4$ and the vapor of 0.6 kg/h of aluminum chloride were introduced separately from one another by means of nitrogen as carrier gas into a mixing chamber. The vapors were mixed with 14.6 standard m$^3$/h of hydrogen and 129 standard m$^3$/h of dried air in the mixing chamber of a burner, fed via a central tube, at the end of which the reaction mixture is ignited, into a water-cooled flame tube and burnt there. The powder formed was subsequently deposited in a filter and treated with water vapor at 400 to 700° C. The powder contained 99% by weight of silicon dioxide and 1% by weight of aluminum oxide. The BET surface area was 173 m$^2$/g. The DBP number was 326 g/100 g of mixed oxide.

To determine the weight ratio (Al$_2$O$_3$/SiO$_2$)$_{surface}$ of the primary particles in a surface layer having a thickness of about 5 nm, XPS analysis was employed. This resulted in a weight ratio (Al$_2$O$_3$/SiO$_2$)$_{surface}$ of 0.0042. The determination of the weight ratio (Al$_2$O$_3$/SiO$_2$)$_{ttl}$ in the total primary particle was carried out by X-ray fluorescence analysis on the powder. It showed a weight ratio (Al$_2$O$_3$/SiO$_2$)$_{ttl}$ of 0.010. This resulted in a value for (Al$_2$O$_3$/SiO$_2$)$_{ttl}$ (Al$_2$O$_3$/SiO$_2$)$_{surface}$ of 2.4.

Isomerization Reaction in Batch Mode

For each experiment, an electrically heated steel autoclave equipped with an internal stirrer was filled with 20 g of 1-tetradecene (feed) and 1 g of catalyst. After closing the reactor, the gas phase in the reactor was exchanged by feeding nitrogen and the pressure was adjusted to about 5 bar. subsequently, the heating of the reactor was started, and the reaction mixture stirred until the end of the desired reaction.

Detailed analysis of the experiments in batch mode was made by $^{13}$C-NMR spectroscopic measurements after reaction stop.

Isomerization Reaction in Continuous Fixed-Bed Operation Mode

The experiments in the continuous operation mode were carried out simultaneously in two setups, each setup consisting of feed vessels, an HPLC-pump, a pre-heating zone, two consecutive tubular fixed-bed reactors located in a heating oven, and a product vessel. Each setup was filled with 6 g of fresh catalyst. The feed consisted of alpha-tetradecene and was pumped via the HPLC pump first through the preheating zone, where the feed liquid is heated to reaction temperature, and then from the bottom to the top through the first and subsequently through the second tubular fixed-bed reactor. This ensured that the reactors were entirely filled with liquid. The reaction mixture was cooled after the reaction zone to ambient temperature and stored in the product tank. The feed tank as well as the product tank were purged with nitrogen.

Reaction Conditions:

WHSV value=3.1 to 4.7 h$^{-1}$ maximum catalyst loading=12 g feed flow rate=0.8 to 1.2 mL/min pressure=atmospheric The reaction product of the continuous operation mode was analyzed in regular intervals by $^{13}$C-NMR to determine the distribution of the C$_{14}$-olefins. The consistency of the analyses was ensured by double measurement of the same sample.

1-Tetradecene Purity

Before starting the experiments, the 1-tetradecenes used as feed were analyzed to determine the initial concentration distributions. Results are shown in Table 1. The term "tetradecane" is abbreviated throughout the tables as "TD".

TABLE 1

Initial composition of 1-tetradecenes used.

| Ex. # | 1-TD [mol %] | 2-TD [mol %] | 3-TD [mol %] | 4-TD [mol %] | 5 + 6 + 7-TD [mol %] | 2-ethyl-1-dodecene [mol %] | 2-propy-1-undecene [mol %] | Dimer [mol %] |
|---|---|---|---|---|---|---|---|---|
| 1 | 95.6 | 0 | 0 | 0 | 0 | 1.6 | 2.5 | 0 |
| 2 | 96.0 | 0 | 0 | 0 | 0 | 1.6 | 2.4 | 0 |
| 3 | 96.3 | 1.5 | 0.4 | 0.2 | 0.4 | 0.6 | 0.6 | 0 |

The initial concentration of 1-tetradecene was about 96 mol % and main side components were 2-ethyl-1-dodecene and 2-propyl-1-undecene. The overall concentration of the branched hydrocarbons was about 4 mol % and no dimers were detected.

Catalytic Materials

The performance of the silicon-aluminum mixed oxide material according to the present invention (Catalyst 3) was compared to catalytic reference materials known to be active in isomerization reactions (Catalyst 1 and Catalyst 2).

Catalyst 1 (Reference): SAPO-39

Catalyst 2 (Reference): Amberlyst 15

Catalyst 3 (invention): silicon-aluminum mixed oxide

Performance Tests in Batch Mode Operation

The experimental conditions for all experiments in the batch mode are summarized in Table 2. Examples with reference catalysts are marked with the term "*)". The term "tetradecene" is abbreviated throughout the tables as "TD".

TABLE 2

Reaction conditions for the experiments in batch mode.

| Ex. # | Catalyst # | m$_{Feed}$ [g] | m$_{cat}$ [g] | Temp. [° C.] | Reaction time [min] |
|---|---|---|---|---|---|
| 4 | — | 775.00 | — | 200 | 380 |
| 5 | 3 | 775.00 | 30.000 | 130 | 842 |
| 6 | 3 | 775.00 | 30.000 | 130 | 977 |
| 7 | 1 | 775.00 | 30.000 | 200 | 1300 |
| 8 | 2 | 20.00 | 1.002 | 110 | 300 |
| 9 | 3 | 20.02 | 1.008 | 200 | 300 |
| 10 | 1 | 20.00 | 1.002 | 200 | 300 |
| 11 | 3 | 20.01 | 0.992 | 200 | 570 |
| 12 | 1 | 20.01 | 1.005 | 200 | 570 |
| 13 | 2 | 20.01 | 1.000 | 110 | 570 |
| 14 | 3 | 20.01 | 0.997 | 130 | 335 |
| 15 | 3 | 20.01 | 1.013 | 175 | 335 |
| 16 | 3 | 20.00 | 1.002 | 225 | 335 |
| 17 | 3 | 20.01 | 0.992 | 245 | 335 |

TABLE 2-continued

Reaction conditions for the experiments in batch mode.

| Ex. # | Catalyst # | $m_{Feed}$ [g] | $m_{cat}$ [g] | Temp. [° C.] | Reaction time [min] |
|---|---|---|---|---|---|
| 18 | 3 | 20.00 | 1.009 | 175 | 56 |
| 19 | 3 | 20.10 | 1.006 | 175 | 117 |
| 20 | 3 | 20.00 | 1.007 | 175 | 191 |

Table 2 gives an overview of the reaction conditions used for the different reactions run under batch mode. At first, a blind test was carried out to determine the influence of the reactor wall and the thermal stability of the used alpha-C14 olefin (see Example 4).

Different reaction conditions were used to determine the catalytic performance of the selected catalysts to identify the best catalyst for the isomerization reaction, to find the optimum reaction conditions for the catalyst and to identify the influence of different feed qualities on the catalytic performance. The amount of feed was approximately 20 g and the amount of catalyst between 0.99 and 1.01 g (see Examples 5-10). Two different reaction times at 300 min and 570 min were compared.

The reaction temperature was varied in the range of 130 to 245° C. for the catalyst of the present invention (see Examples 11-14). Approximately 1 g of catalyst and 20 g of 1-tetradecene were filled in the reactor in each example.

The reaction time was further varied in the range from 56 minutes to 335 minutes for the catalyst of the present invention (see Examples 15-20 and 12). Approximately 1 g of catalyst and 20 g of 1-tetradecene were filled in the reactor in each example.

Results for the Batch Operation Examples

The following Table 3, the results for the above-mentioned examples are regarding conversion and product distribution are shown.

TABLE 3

Results of the double bond distribution of $C_{14}$-olefins in batch reactions.

| Ex # | 1-TD [mol %] | 2-TD [mol %] | 3-TD [mol %] | 4-TD [mol %] | 5 + 6 + 7-TD [mol %] | 2-ethyl-1-dodecene [mol %] | 2-propyl-1-undecene [mol %] | Dimer [mol %] |
|---|---|---|---|---|---|---|---|---|
| 4 | 92.2 | 2.7 | 0.9 | 0.3 | — | 1.6 | 2.3 | — |
| 5 | 86.5 | 6.5 | 1.6 | 1.0 | 0.5 | 1.4 | 2.7 | — |
| 6 | 45.6 | 32.5 | 11.2 | 4.0 | 1.8 | 0.7 | 1.1 | 2.9 |
| 7 | 37.3 | 20.3 | 13.2 | 11.3 | 12.4 | 0.8 | 1.1 | 3.6 |
| 8 | 11.9 | 49.6 | 19.9 | 8.4 | 6.1 | — | — | 4.0 |
| 9 | 1.2 | 14.9 | 14.2 | 17.3 | 41.9 | — | — | 10.5 |
| 10 | 86.5 | 8.8 | 1.0 | — | — | — | — | 3.8 |
| 11 | 0.9 | 12.5 | 11.8 | 15.8 | 38.1 | — | — | 21.0 |
| 12 | 86.8 | 8.1 | 1.1 | — | — | — | — | 4.2 |
| 13 | 1.8 | 34.6 | 22.5 | 16.3 | 15.6 | — | — | 9.0 |
| 14 | 78.8 | 15.5 | 1.7 | — | — | — | — | 4.1 |
| 15 | 1.0 | 16.1 | 14.0 | 15.3 | 29.8 | — | — | 23.8 |
| 16 | 0.8 | 9.7 | 7.7 | 9.9 | 25.7 | — | — | 46.1 |
| 17 | 0.4 | 3.9 | 3.5 | 4.1 | 9.8 | — | — | 78.5 |
| 18 | 42.0 | 35.7 | 10.5 | 3.9 | 2.6 | — | — | 5.4 |
| 19 | 15.9 | 44.5 | 18.3 | 8.8 | 6.8 | — | — | 5.7 |
| 20 | 7.7 | 42.9 | 21.5 | 11.9 | 10.4 | — | — | 5.7 |

Blind Test

The results for the blind test show that the alpha-C14 olefin is thermally stable up to 200° C. as the mole fraction of 1-tetradecene decreased only slightly to 92.2 mol % (see Example 4). The concentration of branched hydrocarbons remained unchanged at about 4 mol % and there was no formation of dimers observed.

Catalyst Variation

Examples 5-7 compare the conversion achieved by using the different catalysts and the double bond distribution obtained thereby. Reaction temperatures were 110° C. for Catalyst 2 (Example 5) and 200° C. for Catalyst 3 (Example 6) and Catalyst 1 (Example 7) and the reaction time was 300 minutes, respectively. For the use of Catalyst 2, a lower temperature had to be chosen, because the Amberlyst resin tends to decompose at higher temperatures and unfavorable dimer formation was observed under such conditions. On the other hand, the conversion at 110° C. for the two other catalyst were considerably slow.

The 1-tetradecene conversions are 87.6%, 98.7% and 9.5% for Examples 5, 6 and 7, respectively. The isomerization with Catalyst 2 showed the highest olefin concentration at 2-tetradecene (49.6 mol %). With increasing the carbon number for the double bond position in the carbon chain, the concentration of the respective internal olefin decreased. The lowest concentration was found for 5+6+7-tetradecene.

For Catalyst 3, under these conditions the highest internal olefin isomer concentrations were found with distribution close to equilibrium. Under equilibrium conditions, one would expect 14.7 mol % for each isomer. Experimentally, this value is nearly reached for the 2-, 3- and 4-isomer. For the 5+6+7-tetradecene lumped isomers, 41.9 mol % were obtained compared to calculated 44.1% at equilibrium. At the same time, the concentration of dimers amounted to moderate 10.5 mol %. Catalyst 1 showed the lowest 1-tetradecene conversion. The residual concentration of 1-tetradecene was 86.5 mol % after the applied reaction time. The mole fraction of 2-tetradecene amounted to 8.8 mol %; the concentration of all other internal olefins was lower than 1.0 mol %.

Examples 8-10 are a repetition of Examples 5-7 by increasing the reaction time from 300 to 570 minutes to investigate the influence of reaction time on equilibrium compositions. Due to the longer reaction time, the conversion of 1-tetradecene increased to 98.1 when using Catalyst 2 (Example 10). The concentration of the more internal double bond position isomers increased as well, but equilibrium composition could not be reached. The highest concentration of internal olefin was found for 2-tetradecene (34.6 mol %) and the mole fraction of dimers increased by a factor of 2.3.

Increasing the reaction time only slightly changed the isomer composition of internal olefins by using Catalyst 3. However, the concentration of dimers increased by a factor of 2. With Catalyst 1, no significant changes in the product composition were observed.

Temperature Variation

For the catalyst of the present invention, further examples were made to show the temperature dependence of 1-TD conversion and isomer distribution respectively (see Examples 6 and Examples 11-14). At 130° C. (Example 11), the conversion of 1-tetradecene was only 17.6%. The highest concentration of internal olefins was found at 2-tetradecene (15.5 mol %). The mole fraction of other internal olefins was negligible. The results at 175° C. (Example 12) and 200° C. (Example 6; shorter reaction time) showed nearly full conversion of approximately 99% and a nearly equal distribution of internal olefins over the carbon chain, i.e. equilibrium conditions are met. With increasing the reaction temperature further, the isomer composition does not change anymore significantly (i.e. equal distribution of the double bond position in the tetradecene except the alpha position), but undesired dimer formation increases significantly. At 245° C., most of the tetradecene is converted into dimers.

Reaction Time Variation

When varying the reaction time (see Examples 12 and 15-20), the conversion of 1-tetradecene increased with increasing reaction time. After 56 minutes, the conversion of 1-tetradecene was 56.1% (Example 15) and increases to 99% after 335 minutes (Example 12). However, the mole fraction of dimers also increased from 4.8 mol % to 23.8 mol % with increasing the reaction time. In all experiments, the maximum mole fraction of internal olefin was found at 2-tetradecene, indicating that chemical equilibration of double bond position has not been reached. Only at 335 minutes (Example 12), the concentration of internal olefins was almost equally distributed over the carbon chain length. However, in this case, the concentration of dimers was already very high (23.8 mol %).

Performance Tests in Continuous Mode Operation

In the continuous fixed bed operation mode, the long-term stability of the catalyst of the present invention was investigated. Four different tests were made with different parameter sets were performed. Two reactors were run simultaneously, and two different flow rates were chosen as initial parameters.

Run 1a (Example 21)

In Run 1a, the 1-tetradecene was flown with 1 mL/min through the reactors filled with the catalyst of the present invention. The weight hourly space velocity amounted to 3.88 $h^{-1}$. The reactor was heated to 180° C. After 11 days, the temperature was reduced to 170° C. and the other parameters kept constant. After 18 days, the flow rate was reduced to 0.8 mL/min (resulting in a WHSV of 3.1 $h^{-1}$). The other parameters were kept constant. The total time-on-stream amounted to 32 days. Table 4 shows the reaction conditions and the conversion of 1-tetradecene as obtained.

TABLE 4

Reaction parameters and conversion X of 1-tetradecene in Run 1a.

| Reaction time [days] | Feed [mL/min] | WHSV [$h^{-1}$] | Temperature [° C.] | Conversion [%] |
|---|---|---|---|---|
| 4 | 1.0 | 3.88 | 180 | 96.7 |
| 6 | 1.0 | 3.88 | 180 | 96.6 |
| 8 | 1.0 | 3.88 | 180 | 95.4 |
| 11 | 1.0 | 3.88 | 180 | 95.0 |
| 13 | 1.0 | 3.88 | 170 | 92.7 |
| 18 | 1.0 | 3.88 | 170 | 89.1 |
| 22 | 0.8 | 3.10 | 170 | 89.9 |
| 27 | 0.8 | 3.10 | 170 | 85.2 |
| 32 | 0.8 | 3.10 | 170 | 85.8 |

The product distribution of the different isomers for the sampling in Run 1a are reported in the following Table 5.

TABLE 5

Results of the double bond distribution of $C_{14}$-olefins in Run 1a.

| Reaction time [days] | 1-TD [mol %] | 2-TD [mol %] | 3-TD [mol %] | 4-TD [mol %] | 5-TD [mol %] | 6 + 7-TD [mol %] | Dimer [mol %] |
|---|---|---|---|---|---|---|---|
| 0 | 96.0 | 0 | 0 | 0 | 0 | 0 | 0 |
| 4 | 3.2 | 25.3 | 18.5 | 17.6 | 12.8 | 15.9 | 6.6 |
| 6 | 3.3 | 26.3 | 18.7 | 17.5 | 12.7 | 15.2 | 6.1 |
| 8 | 4.4 | 28.6 | 19.5 | 16.6 | 12.0 | 13.3 | 5.7 |
| 11 | 4.8 | 29.7 | 19.9 | 16.0 | 11.3 | 12.1 | 6.1 |
| 13 | 7.0 | 37.8 | 21.7 | 14.2 | 8.0 | 6.3 | 5.0 |
| 18 | 10.4 | 42.6 | 21.3 | 11.9 | 5.7 | 4.1 | 4.0 |
| 22 | 9.7 | 42.8 | 22.0 | 11.8 | 5.3 | 4.0 | 4.4 |
| 27 | 14.2 | 46.4 | 20.3 | 9.2 | 3.9 | 2.4 | 3.8 |
| 32 | 13.6 | 45.8 | 20.4 | 9.4 | 4.0 | 2.6 | 4.3 |

After 4 hours on-stream, a high conversion level of 96.7% was obtained at the reactor outlet.

The isomers consisted of a high level of inner double bond positions, the 2-position slightly dominating with 25.3%. With increasing time-on-stream a slight deactivation of the catalyst was observed in Run 1a, which can be seen in a reduced conversion and less equilibrated concentration of the respective inner double bond isomers. When reducing the reaction temperature to 170° C., the conversion was further diminished and the double bond position at the 2-position became more dominating. With increasing time-on-stream, deactivating is increased. After 18 days, the feed rate was reduced to 0.8 mL/min (WHSV=3.1 $h^{-1}$) resulting in a slight conversion increase to 89.9% due to the higher residence time in the catalyst bed. The Isomer composition, however, was not significantly affected. In all conditions, the dimer formation was low and between 6.6% on day 4 and 4.3% after 32 days.

Run 1 b (Example 22)

In Run 1 b, the 1-tetradecene was flown with 0.9 mL/min through the reactors filled with the catalyst of the present invention. The weight hourly space velocity amounted to 3.49 $h^{-1}$. The reactor was heated to 180° C. After 6 days, the flow rate was increased to 1.2 mL/min (WHSV=4.65 $h^{-1}$). The other parameters were kept constant. After 11 days, the reactor temperature was reduced to 170° C. The other parameters were kept constant. The total time-on-stream amounted to 32 days.

The following Table 6 shows the reaction conditions and the conversion of 1-tetradecene as obtained.

TABLE 6

Reaction parameters and conversion X of 1-tetradecene in Run 1b.

| Reaction time [days] | Feed [mL/min] | WHSV [$h^{-1}$] | Temperature [° C.] | Conversion [%] |
|---|---|---|---|---|
| 4 | 0.9 | 3.49 | 180 | 97.0 |
| 6 | 0.9 | 3.49 | 180 | 96.2 |
| 8 | 1.2 | 4.65 | 180 | 95.3 |
| 11 | 1.2 | 4.65 | 180 | 94.8 |
| 13 | 1.2 | 4.65 | 170 | 90.0 |
| 18 | 1.2 | 4.65 | 170 | 88.6 |
| 22 | 0.8 | 3.10 | 170 | 91.6 |
| 27 | 0.8 | 3.10 | 170 | 89.0 |
| 32 | 0.8 | 3.10 | 170 | 88.0 |

The product distribution of the different isomers for the sampling in Run 1 b are reported in the following Table 7.

TABLE 7

Results of the double bond distribution of $C_{14}$-olefins in Run 1b.

| Reaction time [days] | 1-TD [mol %] | 2-TD [mol %] | 3-TD [mol %] | 4-TD [mol %] | 5-TD [mol %] | 6 + 7-TD [mol %] | Dimer [mol %] |
|---|---|---|---|---|---|---|---|
| 0 | 96.0 | 0 | 0 | 0 | 0 | 0 | 0 |
| 4 | 2.9 | 21.6 | 16.4 | 17.9 | 14.6 | 19.1 | 7.5 |
| 6 | 3.6 | 23.7 | 17.9 | 17.0 | 13.7 | 17.0 | 7.0 |
| 8 | 4.5 | 27.7 | 19.1 | 16.8 | 12.1 | 14.0 | 5.9 |
| 11 | 5.0 | 28.4 | 19.2 | 16.1 | 11.6 | 12.8 | 6.8 |
| 13 | 8.7 | 39.3 | 20.7 | 13.7 | 7.0 | 6.0 | 4.5 |
| 18 | 10.9 | 41.0 | 20.7 | 11.5 | 6.3 | 4.6 | 5.2 |
| 22 | 8.0 | 39.3 | 21.3 | 13.0 | 6.6 | 7.5 | 4.5 |
| 27 | 10.5 | 42.2 | 21.3 | 11.3 | 7.1 | 3.6 | 4.0 |
| 32 | 11.5 | 42.4 | 20.7 | 11.3 | 5.4 | 4.1 | 4.7 |

After 4 hours on-stream, a high conversion level of 97% was obtained at the reactor outlet. The isomers consisted of a high level of inner double bond positions, close to equilibrium composition, the 2-position slightly dominating with 21.6%. With increasing time-on-stream, a slight deactivation of the catalyst was also observed in Run 1b, which can be seen in a reduced conversion and less equilibrated concentration of the respective inner double bond isomers. After increase of the feed stream to 1.2 mL/min on day 6, the conversion expectedly decreased, and the isomer composition shifted towards the 2-position. When reducing the reaction temperature to 170° C. after day 11, the conversion was further diminished and the double bond position at the 2-position became still more dominating. After 18 days, the feed rate was reduced to 0.8 mL/min (WHSV=3.1 $h^{-1}$) resulting in a slight conversion increase to 91.6% due to the higher residence time in the catalyst bed. The isomer composition, however, was not significantly affected. In all conditions, the dimer formation was low and between 7.5% on day 4 and 4.7% after 32 days.

Run 2a (Example 23)

In Run 2a, the 1-tetradecene was flown with 1 mL/min through the reactors filled with the catalyst of the present invention. The weight hourly space velocity amounted to 3.88 $h^{-1}$. The reactor was heated to 180° C. After 8 days, the temperature was reduced to 170° C. and the other parameters kept constant. Total time-on-stream amounted to 25 days. The following Table 8 shows the reaction conditions and the conversion of 1-tetradecene obtained.

TABLE 8

Reaction parameters and conversion X of 1-tetradecene in Run 2a.

| Reaction time [days] | Feed [mL/min] | WHSV [h$^{-1}$] | Temperature [° C.] | Conversion [%] |
|---|---|---|---|---|
| 4 | 1.0 | 3.88 | 180 | 93.8 |
| 8 | 1.0 | 3.88 | 180 | 92.1 |
| 13 | 1.0 | 3.88 | 170 | 88.5 |
| 19 | 1.0 | 3.88 | 170 | 84.4 |
| 25 | 1.0 | 3.88 | 170 | 71.5 |

The product distribution of the different isomers for the sampling in Run 2a are reported in the following Table 9.

TABLE 9

Results of the double bond distribution of C$_{14}$-olefins in Run 2a.

| Reaction time [days] | 1-TD [mol %] | 2-TD [mol %] | 3-TD [mol %] | 4-TD [mol %] | 5-TD [mol %] | 6 + 7-TD [mol %] | Dimer [mol %] |
|---|---|---|---|---|---|---|---|
| 0 | 96.0 | 0 | 0 | 0 | 0 | 0 | 0 |
| 4 | 5.9 | 27.3 | 18.3 | 16.0 | 11.5 | 14.5 | 6.5 |
| 8 | 7.6 | 31.5 | 19.3 | 15.3 | 10.4 | 11.1 | 4.9 |
| 13 | 11.0 | 42.3 | 21.3 | 11.2 | 5.5 | 3.7 | 4.9 |
| 19 | 14.9 | 42.7 | 19.1 | 9.5 | 4.1 | 5.6 | 4.1 |
| 25 | 27.3 | 45.4 | 15.1 | 5.2 | 1.8 | 1.3 | 4.0 |

After 4 hours on-stream, a high conversion level of 93.8% was obtained at the reactor outlet. The isomers consisted of a high level of inner double bond positions, the 2-position slightly dominating with 27.3%. With increasing time-on-stream, a slight deactivation of the catalyst was observed, which can be seen in a reduced conversion and less equilibrated concentration of the respective inner double bond isomers. When reducing the reaction temperature to 170° C., the conversion was further diminished and the double bond position at the 2-position became more dominating. With increasing time-on-stream, deactivating was increased. After 25 days, 71.5% of the 1-tetradecene was converted. In all conditions, the dimer formation was low and between 5.9% on day 4 and 4% after 25 days.

Run 2b (Example 24)

In Run 2b, the 1-tetradecene was flown with 0.9 mL/min through the reactors filled with the catalyst of the present invention. The weight hourly space velocity amounted to 3.49 h$^{-1}$. The reactor was heated to 180° C. After 4 days, the flow rate was increased to 1.2 mL/min (WHSV=4.65 h$^{-1}$). The other parameters were kept constant. After 8 days, the reactor temperature was reduced to 170° C. The other parameters were kept constant. Total time-on-stream amounted to 25 days. The following Table 10 shows the reaction conditions and the conversion of 1-tetradecene obtained.

TABLE 10

Reaction parameters and conversion X of 1-tetradecene in Run 2b.

| Reaction time [days] | Feed [mL/min] | WHSV [h$^{-1}$] | Temperature [° C.] | Conversion [%] |
|---|---|---|---|---|
| 4 | 0.9 | 3.49 | 180 | 96.1 |
| 8 | 1.2 | 4.65 | 180 | 97.0 |
| 13 | 1.2 | 4.65 | 170 | 95.6 |

TABLE 10-continued

Reaction parameters and conversion X of 1-tetradecene in Run 2b.

| Reaction time [days] | Feed [mL/min] | WHSV [h$^{-1}$] | Temperature [° C.] | Conversion [%] |
|---|---|---|---|---|
| 19 | 1.2 | 4.65 | 170 | 92.0 |
| 25 | 1.2 | 4.65 | 170 | 90.1 |

The product distribution of the different isomers for the sampling in Run 2b are reported in the following Table 11.

TABLE 11

Results of the double bond distribution of C$_{14}$-olefins in Run 2b.

| Reaction time [days] | 1-TD [mol %] | 2-TD [mol %] | 3-TD [mol %] | 4-TD [mol %] | 5-TD [mol %] | 6 + 7-TD [mol %] | Dimer [mol %] |
|---|---|---|---|---|---|---|---|
| 0 | 95.7 | 0 | 0 | 0 | 0 | 0 | 0 |
| 4 | 3.7 | 19.7 | 16.4 | 17.2 | 15.3 | 19.2 | 8.5 |
| 8 | 2.9 | 23.6 | 17.2 | 17.8 | 13.2 | 17.4 | 8.0 |
| 13 | 4.2 | 30.5 | 19.8 | 16.8 | 11.5 | 11.7 | 5.4 |
| 19 | 7.7 | 34.8 | 20.0 | 13.1 | 7.5 | 12.3 | 4.6 |
| 25 | 9.5 | 39.0 | 21.1 | 13.4 | 7.1 | 6.2 | 3.6 |

After 4 hours on-stream, a high conversion level of 96.1% was obtained at the reactor outlet. The isomers consisted of high level of inner double bond positions, close to equilibrium composition, the 2-position slightly dominating with 19.7%. After increase of the feed stream to 1.2 mL/min on day 4, the conversion did not decrease significantly but the isomer composition shifted towards the 2-position (23.6%). When reducing the reaction temperature to 170° C. after day 8, the conversion was further diminished and the double bond position at the 2-position became still more dominating. Under all conditions, the dimer formation was low and between 8.5% on day 4 and 3.6% after 25 days.

CONCLUSIONS

According to the present invention, the reaction temperature and mean WHSV are the important parameters in the isomerization process when using the silicon-aluminum mixed oxide catalyst. The results achieved with the four runs showed that a reaction temperature of about 180° C. leads to a conversion from the used alpha-olefin to inner olefins of about 95% with good distribution of the inner olefins over the carbon chain and a dimer fraction of about 6.5 to 8.5 mol %. The dimer fraction could be decreased well below 5 mol % by reducing the reaction temperature to 170° C.

The equilibrium composition of the internal olefins shifted towards lower double bond positions with decreasing the catalytic activity over the time. The used catalyst showed good performance after 32 days long term stability test.

The invention claimed is:

1. A method, comprising:
   reacting, by isomerization, at least one alpha-olefin comprising 10 to 20 carbon atoms with a silicon-aluminum mixed oxide composition as a catalyst, to obtain an internal olefin;
   wherein the silicon-aluminum mixed oxide composition consists of:
   75 to 99.99% by weight of silicon dioxide (calculated as $SiO_2$); and
   0.01 to 25% by weight of aluminum oxide (calculated as $Al_2O_3$).

2. The method according to claim 1, wherein the silicon-aluminum mixed oxide composition has a BET surface area from 50 to 250 $m^2/g$.

3. The method according to claim 1, wherein the silicon-aluminum mixed oxide composition consists of:
   85 to 99.99% by weight of silicon oxide (calculated as $SiO_2$); and
   0.01 to 15% by weight of aluminum oxide (calculated as $Al_2O_3$).

4. The method according to claim 1, wherein the silicon-aluminum mixed oxide composition is prepared by flame hydrolysis.

5. The method according to claim 1, wherein the at least one alpha-olefin comprises 14 to 16 carbon atoms, or the at least one alpha-olefin comprises a mixture of alpha-olefins comprising 14 to 16 carbon atoms.

6. The method according to claim 1, wherein the at least one alpha-olefin is an alpha-tetradecene comprising at least 90% by weight of mono-olefinic linear alpha-olefins.

7. The method according to claim 1, wherein the reacting comprises:
   (a) providing the catalyst in a reaction zone of a reactor;
   (b) inerting and tempering the reactor to a reaction temperature;
   (c) continuously feeding the at least one alpha-olefin first through a preheating zone and then through the reaction zone to a reaction mixture, by controlling temperature, pressure and weight hour space velocity (WHSV);
   (d) optionally, if the reactor is a slurry reactor, removing the catalyst from the reaction mixture at a reaction outlet;
   (e) cooling the reaction mixture after the reaction zone to a temperature for further processing; and
   (f) optionally, collecting an isomerized product comprising the internal olefin; and/or
   (g) optionally, removing undesired by-products.

8. The method according to claim 7, wherein the catalyst consists of shaped bodies prepared by a shaping process from the silicon-aluminum mixed oxide composition, a binder and a temporary assistant.

9. The method according to claim 7, wherein the reaction temperature is in the range of 130 to 340° C.

10. The method according to claim 7, wherein the weight hour space velocity (WHSV) is in the range of 3.0 to 5.5 $h^{-1}$.

11. The method according to claim 1, wherein a conversion rate of the at least one alpha-olefin is 95% or higher.

12. The method according claim 1, wherein an amount of dimer in the isomerized product is 5 mol % or lower.

13. An isomerized product of at least one alpha-olefin comprising 10 to 20 carbon atoms, or a mixture thereof, prepared by a method comprising:
   (a) providing a catalyst in a reaction zone of a reactor;
   (b) inerting and tempering the reactor to a reaction temperature;
   (c) continuously feeding the at least one alpha-olefin first through a preheating zone and then through the reaction zone to a reaction mixture, by controlling temperature, pressure and weight hour space velocity (WHSV);
   (d) optionally, if the reactor is a slurry reactor, removing the catalyst from the reaction mixture at a reaction outlet;
   (e) cooling the reaction mixture after the reaction zone to a temperature for further processing; and
   (f) optionally, collecting the isomerized product; and/or
   (g) optionally, removing undesired by-products.

14. The isomerized product according to claim 13, wherein an amount of dimer is 5 mol % or lower.

15. The method according to claim 2, wherein the silicon-aluminum mixed oxide composition has a BET surface area from 100 to 200 $m^2/g$.

16. The method according to claim 5, wherein the at least one alpha-olefin comprises 14 carbon atoms.

17. The method according to claim 7, wherein the reactor is a fixed-bed reactor.

18. The method according to claim 7, wherein in (g), the by-products are removed by distillation, rectification, vacuum distillation, or membrane separation.

19. The method according to claim 9, wherein the reaction temperature is in the range of 160 to 190° C.

20. The method according to claim 10, wherein the weight hour space velocity (WHSV) is in the range of 3.5 to 3.7 $h^{-1}$.

21. A method, comprising:
   reacting, by isomerization, at least one alpha-olefin comprising 10 to 20 carbon atoms with a silicon-aluminum mixed oxide composition as a catalyst, to obtain an internal olefin;
   wherein the silicon-aluminum mixed oxide composition consists of:
   75 to 99.99% by weight of silicon dioxide (calculated as $SiO_2$);
   0.01 to 25% by weight of aluminum oxide (calculated as $Al_2O_3$); and
   wherein the silicon-aluminum mixed oxide composition has a BET surface area from 50 to 250 $m^2/g$.

22. The method according to claim 1, wherein surfaces of particles of the silicon-aluminum mixed oxide are largely or completely free of pores.

23. The method according to claim 1, further comprising:
   providing the catalyst in a fixed-bed reactor; and
   wherein the silicon-aluminum mixed oxide composition has a BET surface area from 50 to 250 $m^2/g$.

24. The method according to claim 1, wherein the silicon-aluminum mixed oxide has a dibutyl phthalate (DBP) number of from 300 to 350.

* * * * *